United States Patent [19]

Gardner et al.

[11] 4,263,413
[45] Apr. 21, 1981

[54] HALF ESTERS OF ORGANIC POLYOLS AND A PROCESS FOR THEIR PRODUCTION

[75] Inventors: Hugh C. Gardner, Somerville; Robert J. Cotter, Bernardsville, both of N.J.

[73] Assignee: Union Carbide Corporation, New York, N.Y.

[21] Appl. No.: 129,884

[22] Filed: Mar. 27, 1980

Related U.S. Application Data

[63] Continuation-in-part of Ser. No. 34,995, May 1, 1979, abandoned.

[51] Int. Cl.³ .............................................. C08G 63/76
[52] U.S. Cl. .................................. 525/34; 260/40 R; 525/36; 525/43; 525/48; 525/49; 528/300
[58] Field of Search .................. 525/34, 36, 43, 48, 525/49; 528/300; 260/40 R

[56] References Cited

U.S. PATENT DOCUMENTS

| | | | |
|---|---|---|---|
| 2,813,055 | 11/1957 | Nischk et al. | 525/34 |
| 3,320,336 | 5/1967 | Duke et al. | 528/300 X |
| 3,449,467 | 6/1969 | Wynstra | 528/300 X |
| 3,766,129 | 10/1973 | Pesez | 260/40 R |
| 3,784,586 | 1/1974 | Thomas et al. | 525/21 |
| 3,814,724 | 6/1974 | Suzuki et al. | 260/40 R |
| 3,957,906 | 5/1976 | Buzbee et al. | 525/48 |
| 4,137,279 | 1/1979 | Smith et al. | 525/49 |

*Primary Examiner*—Lucille M. Phynes
*Attorney, Agent, or Firm*—Donald M. Papuga

[57] ABSTRACT

The invention comprises a homogeneous liquid mixture of (a) a half ester of an organic polyol characterized by the following empirical formula:

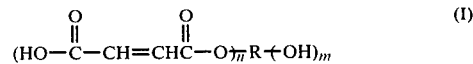

wherein n is a number having an average value of about 1.8 to less than about 4, m is equal to the free valence of R less the average value of n, R is the hydroxyl-free residue of an organic polyol which contained from 2 to 4, inclusive, hydroxyl groups, OH, in formula (I), (b) maleic anhydride, (c) an ethylenically unsaturated monomer which forms a liquid homogeneous mixture with and is copolymerizable with the half ester and maleic anhydride, and (d) a basic compound.

30 Claims, No Drawings

HALF ESTERS OF ORGANIC POLYOLS AND A PROCESS FOR THEIR PRODUCTION

This application is a continuation-in-part application of U.S. patent application Ser. No. 034,995, filed May 1, 1979 now abandoned.

This invention is directed to polymerizable compositions which can be employed in the manufacture of composite structures, and particularly in the manufacture of fiber-reinforced plastic compositions (FRP). The polymerizable composition of this invention is a mixture of low molecular weight monomeric structures which when subjected to free radical polymerization mechanisms yield a thermoset crosslinked composition which possesses many of the attributes of thermosetting polyester resins, particularly when utilized in FRP applications.

Conventional polyester resins are mixtures of unsaturated polyesters in styrene. The polyesters are typically produced by the condensation polymerization of maleic anhydride or maleic acid with a polyol, typically a diol. The resulting polyester product contains a certain concentration of unsaturation in the backbone of the polymer which is derived from the initial unsaturated acid or its anhydride. Typical commercial polyesters can be as simple as poly(propylenemaleate) or as complex as the co-reaction of maleic anhydride or acid, phthalic anhydride and a mixture of diols.

An unsaturated polyester widely used in automotive applications is made from maleic anhydride and propylene glycol. However, due to the requirements of increased toughness, newer commercial polyesters utilized in automotive applications are frequently more complex in their structure. They are typiclly derived from the co-reaction of maleic anhydride, isophthalic or terephthalic acids or their esters, and glycols such as, propylene glycol, diethylene glycol, dipropylene glycol and/or ethylene glycol. Maleic anhydride or acid is a starting component in these polyesters. During the manufacture of these polyesters or in the curing thereof, a considerable amount of isomerization of the maleate into the fumarate form occurs. Thus, most of these resins contain fumarate type double bonds as the predominant source of unsaturation in their backbone. The molecular weight (Mn) of these polyesters can range from about 500 to 5,000. However, most of the commercial polyesters have molecular weights (Mn) of from about 1,300 to 2,500.

Fiberglass has been widely used as a reinforcement in the manufacture of thermoset molded articles. These types of articles have been termed "Glass Reinforced Plastics" (GRP) and "Glass Fiber Reinforced Plastics" (GFR). The fiberglass content in these thermoset molded articles ranges from about 15 to about 75-80 weight percent. Polyester resins are used primarily as the resin component in these glass reinforced thermoset plastics.

The aforedescribed polyester resins have been employed in the manufacture of a variety of glass reinforced products by different types of processes. The processes of forming glass reinforced products are generally in two categories, i.e., wet lay up and thickened processes. Wet lay up processes include the following: pre-impregnation of a fibrous mass with resin, followed by compression molding; preforming in which cut fiber and resin are sprayed onto a mold form itself; mat molding, in which liquid resin is poured onto a mat while the mat is disposed in a compression mold; bulk molding, in which a non-thickened mixture of stapler fiber and polyester resin are poured into a mold.

In thickened processes, polyester resin carboxylic acid groups react with an inorganic alkaline earth metal oxide or hydroxide such as, magnesium oxide and calcium hydroxide, to increase the viscosity of the fiber containing resin so that it has a non-liquid paste-like quality. The resin can then be handled and deposited within the framework of a mold to achieve a more uniform and more convenient molding. Thus, sheet molding compounds (SMC) are formed by depositing resins across a layer of cut fiberglass fibers randomly deposited upon a polyethylene film. The polyethylene film is sandwiched by another layer of polyethylene film and the combination is fed through nip rollers which blends the polyester resin within the fibrous mat to form a sheet. The sheet is allowed to stand so that reaction occurs between the carboxy groups of the polyester resin and the alkaline earth metal oxide filler. The resin increases in viscosity and it can then be easily handled in the molding procedure. This same technique can be utilized in producing bulk molding compounds (BMC). Alkaline earth metal is added to the bulk molding composition in an amount sufficient to thicken the composition to a desired viscosity so that it can be more readily handled. The thickened bulk molding compounds are employed in transfer and injection moldings.

Thickened bulk molding compounds, however, have not been widely used in injection molding since their viscosities are normally higher than is desirable for effective molding, and the equipment required to mold the high viscosity thickened bulk molding compound is extremely expensive, large, and cumbersome to operate. A further advantage in using thickened bulk molding compounds in an injection molding process is that the fibers must be of very short length in order to effectively distribute the fiber throughout the mold. The short lengths of the fibers minimizes the reinforcement so that the resulting molded article does not have optimum performance characteristics particularly, strength properties. Moreover, such short fibers tend to become oriented along the flow of the compound in the mold thereby reducing the strength of the molded article in the direction transverse of the flow.

However, polyester resin systems have been developed which provide good surface properties to the molded product. These polyester resin systems are used in the manufacture of "Class A" molded products employed in the automotive industry. These products have extremely low profile surfaces which are free of warpage, undulations, and fiber protrusions. This low profile results from adding a low profile additive to the BMC or SMC formulation. A low profile additive is a thermoplastic compound which contains a sufficient number of carboxylic acid groups allowing it to become intricately bound into the resin system so that it is not exuded therefrom. Low profile additives can also be utilized in wet lay up processes to form glass reinforced products. Non-carboxylated containing thermoplastics are very effective low profile additives for resin systems used in the wet lay up process although carboxylated thermoplastics presently available for the same purpose can be so utilized.

The glass fiber reinforced polyester resin systems which are used to form "Class A" products typically contain from about 15 to 40 weight percent of glass fiber. These fiber reinforced polyester resin systems are used to mold products where surface appearance is very important, but strength properties are not necessarily as important. However, structural products are expected to have high strength properties. For example, "Class A" products cannot be used effectively in automotive applications where structural integrity is a critical factor. Recently, a series of glass fiber reinforced polyester resins have been developed which utilize the thickening characteristics of SMC, BMC, and the like, but which contain extremely high concentrations of glass fiber. For example, a series of polyester compositions containing from about 50 to about 75 weight percent of glass fibers have been developed. These polyester compositions can be used in making molded products, but typically, they do not possess the desirable surface characteristics which provides a "Class A" product. However, their strength characteristics, which is supplied by the high concentration of glass fibers, provides unique markets for these glass fiber reinforced polyester resins. The fibers in these reinforced resins are either unidirectionally aligned, as from continuous filament tow, or are randomly distributed in long fibers in a polyester mat, or from a combination thereof, to supply enhanced multidirectional strength to the molded article. The high glass fiber containing polyester resins are sheet molding compounds XMC, HMC (XMC and HMC are trademarks of PPG Industries, Inc.) and MSMC-R-Fiber content such as 50–65, (trademarks of Owens Corning Fiberglass Corp.). These high glass fiber content resin systems are molded only by compression molding procedures.

Conventional unsaturated polyesters comprise the reaction product of an unsaturated polycarboxylic acid (or its anhydride should the same exist) and a polyhydric alcohol. Such polyesters are dissolved in an ethylenically unsaturated monomer such as styrene, alpha-methylstyrene, ethyl acrylate, diallyl phthalate, triallyl cyanurate and the like. Of the various polyesters in which the reaction product is solely that of a dicarboxylic acid and a dihydric alcohol, essentially any combination of dicarboxylic acid and dihydric alcohol will be soluble in the ethylenically unsaturated monomer such as styrene. It has been indicated that poly(ethylene maleate) or poly(ethylene fumarate) are insoluble in styrene. On the other hand, poly(propylene maleate) and poly(propylene fumarate) are clearly established as being soluble in styrene. Thus, the structural characteristics of a dihydric alcohol is a factor in determining solubility of the resulting polyester in styrene.

Molecular structures derived from the reaction of a dicarboxylic acid and a dihydric alcohol are described by Thomas et al., U.S. Pat. No. 3,784,586, patented Jan. 8, 1974. Thomas et al depicts the reaction of two moles of maleic anhydride with one mole of dihydric alcohol to produce a composition which is characterized as a copolymerizable oligoester having maleic acid end groups in combination with vinyl monomers and a method for preparing the composition. According to the patent, maleic anhydride is reacted with one or more polyhydroxylated compounds in the ratio of a mole of maleic anhydride per hydroxyl group of the polyhydroxylated compound or compounds at a temperature within the range of 50° C. to 100° C. until the reaction mixture has a hydroxyl number below or equal to 20. Thereafter, at a temperature between room temperature and 100° C., a cross-linking vinyl monomer and a polymerization inhibitor are added. According to the patent, it is essential that the reaction temperature between maleic anhydride and polyhydroxylated compound not exceed 100° C.

However, in using the proportions of 2,2,4-trimethyl-1,3-pentanediol and maleic anhydride specified in Example I of that patent, it has been determined that when this mixture is heated at a temperature in excess of 100° C., the resulting product will yield a precipitate on standing. Thus, it is assumed that the patentees believed that the fumarate was formed when the reaction was conducted at a temperature in excess of 100° C. This yielded an insoluble product which precipitated.

Further, careful duplication of Example I of thepatent has demonstrated that in practicing the process, the mixture of products obtained is quite complex, containing the mono- and bis(maleate) half esters of the polyhydroxylated compound, polyesters resulting from the reaction of these half esters with compounds containing residual hydroxyl groups, fumarate half esters, unreacted maleic anhydride and maleic acid.

The procedure in Example 1 of U.S. Pat. No. 3,784,586 states that the reaction mixture had a hydroxyl number of 20 after 4 hours at 80° C. For this to occur, 93.9 percent of the maleic anhydride must have reacted with the hydroxyl groups on the diol.

In repeating Example 1 of U.S. Pat. No. 3,784,586, it has been found that after 4 hours at 80° C., about 7 mole percent of the maleic anhydride is converted to fumarate half esters which are soluble in styrene. Significantly about 23 mole percent of the maleic anhydride remains unreacted. This large amount of unreacted maleic anhydride indicates that a reduced amount of bis half esters are present. Therefore, the composition of U.S. Pat. No. 3,784,586 contains undesirable amounts of the mono(half ester) of the polyhydroxylated compound. In addition, the composition contains an undesirable amount of unreacted maleic anhydride. These undesirable amounts result in insufficient cross-linking of the total composition set forth as desirable in the patent. This is evidenced by solvent swelling of cured samples of the products produced in accordance with the patent.

When the reaction product from 2,2,4-trimethyl-1,3-pentanediol is mixed with styrene, a precipitate of maleic acid appears after a few days. This precipitate can block pumps, valves and lines used in the equipment which utilizes the compositions. Since the maleic acid is formed from the maleic anhydride, it reduces the amount of maleic anhydride available to form bis(half esters) of the diol. This also results in reduced cross-linking densities in cured compositions containing, for example, styrene. Maleic acid results from hydrolysis of maleic anhydride.

When Example 1 of U.S. Pat. No. 3,784,586 was duplicated, a portion of the 2,4,4-trimethyl-1,3-pentanediol/maleic anhydride reaction mixture was removed immediately before the addition of styrene. After standing for 16 days at room temperature it was analyzed by NMR spectroscopy. It was determined that 8 percent of the original charge of maleic anhydride had been converted to maleic acid.

THE INVENTION

This invention is directed to a composition of half esters of organic polyols, maleic anhydride, ethylenically unsaturated monomer, and a base. Also, this invention concerns a process for producing a composition containing half esters of organic polyols, maleic anhydride, a base and optionally, a monoethylenically unsaturated monomer.

The composition of this invention comprises a homogeneous liquid mixture of (a) a half ester of an organic polyol characterized by the following empirical formula:

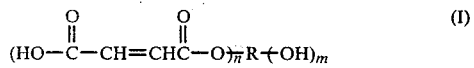

wherein n is a number having an average value of about 1.8 to less than about 4, m is equal to the free valence of R less the average value of n, R is the hydroxyl-free residue of an organic polyol which contained from 2 to 4, inclusive, hydroxyl groups, OH, in formula (I), (b) maleic anhydride, (c) an ethylenically unsaturated monomer which forms a liquid homogeneous mixture with and is copolymerizable with the half ester and maleic anhydride, and (d) a basic compound.

The composition of this invention is essentially free from the diester formation which is prevalent in the process of U.S. Pat. No. 3,784,586. As a result, the polymers of this invention contain less monoolefinic monomers, such as maleic anhydride or the mono half ester of the polyhydroxylated compound than the composition of U.S. Pat. No. 3,784,586. Thus, the composition of this invention achieves a greater degree of cross-linking than the composition of that patent. Moreover, the composition of this invention is a homogeneous liquid mixture which does not form a precipitate on standing as is formed by the composition of said patent. The precipitate formed by the composition produced by the process as set forth in U.S. Pat. No. 3,784,586 is crystals of maleic acid. The precipitate could create substantial processing problems in the manufacture of cross-linked cureable products.

Compared to the composition described in Example 1 of U.S. Pat. No. 3,784,586, the compositions of this invention display reduced swelling in organic solvents and reduced water sorption tendencies. These properties are highly desirable for applications where attack by solvents or environmental moisture are likely to occur. One particular application where these improved properties are highly desirable is in fiber reinforced parts for automobiles, buses, trains, aircraft, and other vehicles.

With respect to the composition of this invention, the half ester of the organic polyol is characterized by the following empirical formula:

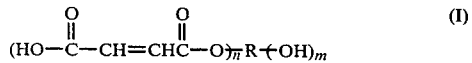

This half ester is formed by the reaction of maleic anhydride and an organic polyol. The reaction product contains at least 1.8 ester groups. If the polyol contains 4 hydroxyl groups, the reaction product can possess up to 4 half ester groups. If the number of half ester groups is less than the number of hydroxyl groups available from the polyol, the reaction product will contain residual hydroxyl groups. Typically, the maleic anhydride content of the composition does not exceed a total of about 10 mole percent of the amount of maleic anhydride employed in producing the half ester.

The organic polyol which is reacted with the maleic anhydride to form the half ester depicted by empirical formula (I), is typically a polyol which contains at least two carbon atoms and which may contain from 2 to 4, inclusive, hydroxyl groups. These polyols include alkane diols, triols, tetraols, aliphatic ether containing diols, triols, tetraols, cycloaliphatic containing diols, triols, and tetraols, and aromatic containing diols, triols, and tetraols, and the like. Specific illustrations of organic polyols suitable in the practice of this invention include the following: ethylene glycol, diethylene glycol, 2,2,4-trimethyl-1,3-pentane diol, dipropylene glycol, propylene glycol, polypropylene glycol having an average molecular weight of about 150 to about 600, triethylene glycol, 1,4-cyclohexane dimethanol, neopentyl glycol, 2,2-dimethyl-3-hydroxypropyl 2,2-dimethyl-3-hydroxypropionate, triethanolamine, 1,3-butanediol, tetraethylene glycol, 2,2-bis(4-hydroxyphenyl)propane and the ethylene and propylene oxide adducts of 2,2-bis(4-hydroxyphenyl)propane, pentaerythritol, erythritol, glycerine, trimethylol propane, 1,4-butanediol, 1,6-hexanediol, the polycaprolactone ester of a polyol in which from about 1 to about 5, preferably from about 1.5 to about 4.0 moles of caprolactone are esterified with a polyol, such as trimethylol propane or diethylene glycol, preferably the polycaprolactone ester of a polyol is the polycaprolactone ester of trimethylol propane in which about 1.5 moles of caprolactone are reacted with trimethylol propane or the polycaprolacetone ester of trimethylol propane where about 3.6 moles of caprolactone are esterified with trimethylol propane, 2-ethyl-1,3-hexanediol, 1,5-pentanediol, tripropylene glycol, 2,2-bis(4-hydroxycyclohexyl)-propane, 1,2,6-hexane triol, 1,3-propane diol, and the like. The most preferred organic polyols are 2,2-dimethyl-3-hydroxypropyl 2,2-dimethyl-3-hydroxypropionate, and 2,2,4-trimethyl-1,3-pentanediol. The use of mixtures of the aforementioned polyols in producing half esters which are soluble in ethylenically unsaturated monomers such as styrene is very desirable. Whereas low cost diols such as 1,2-propylene glycol and diethylene glycol afford half esters with maleic anhydride which are insoluble in styrene, it has been found that mixtures of diols such as those containing said glycols with, for example, 2,2,4-trimethyl-1,3-pentanediol afford half ester compositions which are soluble at room temperature. These compositions can be conveniently utilized in commercial practice.

The ethylenically unsaturated monomer employed in the composition of this invention is one which forms a liquid homogeneous mixture with maleic anhydride and the half ester structure depicted by formula (I) above. In addition, the ethylenically unsaturated monomer has to be copolymerizable with both maleic anhydride and the half ester.

Suitable ethylenically unsaturated monomers which may be employed in the practice of this invention are one or more monomers which contain a —CH=C< group, and preferably a CH$_2$=C< group. These monomers include styrene and its derivatives and homologues, diallyl phthalate, divinylbenzene, acrylic acid or methacrylic acid and their derivatives such as their esters, amides or nitriles, e.g. methyl acrylate, methyl methacrylate, n-butyl methacrylate, acrylamide, methacrylamide, acrylonitrile, methacrylonitrile, and the like. Also, the monomers include vinyl ethers and esters, e.g. vinyl acetate, vinyl propionate, methyl vinyl ether, and the like, triallyl cyanurate, 1,3-butanediol dimethacrylate, and the like. Mixtures of the aforementioned monomers may be effectively employed in the practice of this invention.

The most preferred ethylenically unsaturated monomer contemplated in the practice of this invention is styrene since it has the most significant commercial utilization for such purposes. To determine whether or not a given ethylenically unsaturated monomer forms a liquid homogeneous mixture with maleic anhydride and the half ester, it is combined with maleic anhydride and the half ester at a temperature of from about 20° to about 70° C., utilizing the proportions of each as specified hereinafter.

In the practice of this invention, the structural characteristics of the polyol, the base and the amount thereof used in the reaction all determine the solubility of the reaction product of the polyol and maleic anhydride in the ethylenically unsaturated monomer. The examples, infra, describe how the optimum solubility of the reaction product of the polyol and maleic anhydride is determined from the nature of the polyol and base.

The compositions of this invention contain a mole ratio of half ester to maleic anhydride ranging from about 9:1 to about 200:1, preferably from about 10:1 to about 100:1. In the most typical and desirable embodiment, the mole ratio of half ester to maleic anhydride is from about 12:1 to about 30:1. The mole ratio of ethylenically unsaturated monomer to half ester ranges from about 0.6 to about 6:1, preferably from about 1:1 to about 4:1.

In the most typical and desirable embodiment, the mole ratio of ethylenically unsaturated monomer to half ester ranges from about 1.1:1 to about 3:1.

The compositions of this invention are desirably produced by affecting an intermixture of maleic anhydride, an organic polyol containing from 2 to 4 hydroxyl groups, and a ethylenically unsaturated monomer. Also, a base is added to the maleic anhydride, organic polyol and ethylenically unsaturated monomer as will hereinafter be described.

The basic compound is selected from an amine or a metal salt of an alcohol or carboxylic acid, or a metal oxide or hydroxide.

The metal salt of the alcohol includes sodium methoxide, potassium ethoxide and lithium isopropoxide. The metal salt of a carboxylic acid includes sodium acetate and potassium benzoate. The metal oxide or hydroxides include the alkali metal hydroxides such as potassium hydroxide, and sodium hydroxide. Magnesium oxide is an example of a suitable metal oxide. Characteristic of all the bases which are suitable for use in this invention is that when 1 gram of the basic compound is dissolved in 100 milliters of water the pH is greater than 7.

A preferred basic compound is a secondary or tertiary amine. These amines have a $pK_b$ in the range of 3 to 12.

Amines suitable for use in the practice of this invention include the following:

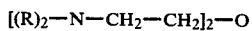

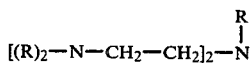

-continued

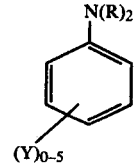

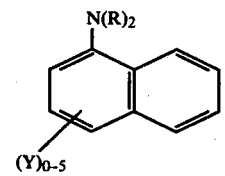

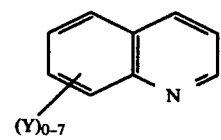

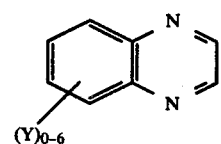

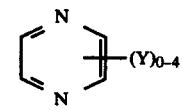

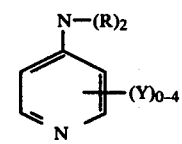

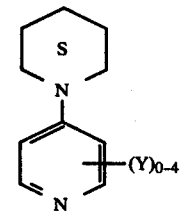

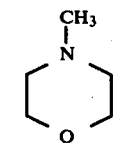

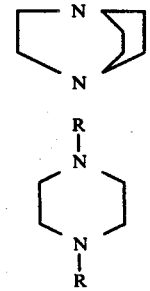

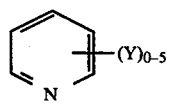

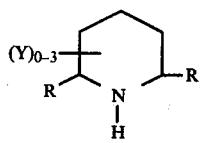

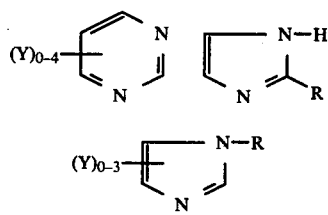

wherein the R's are independently selected from alkyl of 1 to 8 carbon atoms such as $CH_3$, $C_2H_5$, $C_3H_7$, $C_4H_9$, and aralkyl of 7 to 15 carbon atoms such as

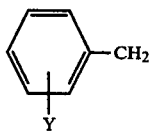

Y is independently selected from alkyl of 1 to 4 carbon atoms, alkoxy of 1 to 4 carbon atoms and halogen.

Additional amines suitable for use herein include 1,5-diazabicyclo[5.40]-undec-5ene; 1,5-diazabicyclo[4.3.0]-non-5-ene. The base is used in amounts of from about 0.01 to about 5 and preferably, from about 0.05 to about 2 weight percent based on the combined weight of the polyol and the maleic anhydride used in making the compositions of this invention.

The compositions of this invention are homogeneous liquid mixtures at temperatures ranging from about 20° C. to about 70° C. Typically, the liquid mixtures of this invention possess room temperature viscosities in the range of about 1 to about 500 centipoises with 40 weight percent of an ethylenically unsaturated monomer, such as styrene. Preferably, with this monomer level, the solution viscosities are between about 5 and about 300 centipoises. In contrast, the viscosities of commercial unsaturated polyester resins are typically 500 to 3000 centipoises.

The bis(half ester) oligomers in the compositions of this invention have molecular weights which range from about 250 to about 900. The number average molecular weights of oligomers in commercial unsaturated polyester resins typically range from about 1300 to about 2500.

The acid numbers of the compositions of this invention range from about 70 to about 500 when measured by the pyridine/methanol mixed solvent method. Preferably the acid number is between about 85 to about 300. Very few commercial unsaturated polyester resins contain an acid number in excess of 50, and in most cases the acid number will range from 15 to about 40.

The process of this invention is carried out at temperatures of from about 15° C. to about 160° C., preferably from 25° C. to about 130° C. The sequence in which the maleic anhydride, polyol, and unsaturated monomer are combined depends on the reaction temperature.

If the ethylenically unsaturated monomer is present during the reaction between the maleic anhydride and the organic polyol, then the reaction temperature should be below the temperature at which maleic anhydride will copolymerize with the ethylenically unsaturated monomer. This temperature is below 60° C.

If the composition of this invention is prepared above about 60° C., then it is desirable to first react the maleic anhydride and the polyol. After about 70 percent of the maleic anhydride has reacted, the ethylenically unsaturated monomer is added. The temperature of the liquid body is rapidly reduced to the desired temperature or to room temperature. The lower temperature is optional and is dependent upon the method used to carry out the process, the type of equipment being used and the manner in which the composition produced will be utilized. The base can be added to either the solution of polyol, maleic anhydride, and unsaturated monomer at a temperature below 60° C. or to a mixture of the polyol and maleic anhydride alone at temperatures above about 40° C. The formation of the half ester is an exothermic reaction. If the latter reaction mode is used, it is desirable to cool the reaction mixture before adding the unsaturated polymerizable monomer to the reaction mixture. This is desirably carried out at temperatures below about 120° C. and after 70 percent of the maleic anhydride has reacted.

In carrying out the process of this invention, the reaction equilibrium between maleic anhydride and organic polyol favors maximum reaction of the maleic anhydride at the lowest temperature. When affecting the reaction at elevated temperature, viz, 80° C., an equilibrium composition in which about 80 percent of the maleic anhydride is reacted with the organic polyol to produce the half ester may be achieved within a reasonable time period. When the reaction mixture is cooled to about room temperature, viz, 23° C., more maleic anhydride reacts with the organic polyol and a conversion of more than about 91 mole percent of maleic anhydride is achieved.

One consideration in the preparation of the compositions of this invention is the degree of isomerization of the maleate half ester to the fumarate form.

In the practice of this invention, it is desirable that not more than about 50 mole percent of the maleate is converted into the fumarate structure and preferably, not more than about 30 mole percent.

The rate at which the maleate structure is converted to the fumarate structure is dependent upon a number of factors which include: the time-temperature history of the reaction mixture, the type of polyol used and the type of amine catalyst employed. With some polyols the rate of isomerization is rapid at relatively low temperature, i.e., about 80° C., whereas with other polyols this same rate is not realized until a temperature of about 130° C. is reached. Thus there is no specific temperature which can be specified to predict the degree of isomerization of the maleate half ester to the fumarate half ester for all polyols. In general, the longer the reaction mixture is heated at a given temperature, the greater the amount of fumarate structures which are produced. The rate of isomerization increases with increasing reaction temperature.

When elevated temperatures, such as those in excess of 90° C. are employed, another factor must be considered, i.e., the condensation reaction of half esters with any free hydroxyl from the polyol results in condensation products having molecular weights higher than the half ester. This is very undesirable in the practice of this invention. Thus, when elevated reaction temperatures are used, it is desirable to carefully monitor the reaction to avoid the formation of these diesters.

When the compositions of this invention are made in the presence of an ethylenically unsaturated monomer, at room temperature, the rate of isomerization of maleate to fumarate is sufficiently slow so that essentially no fumarate is formed.

The present reaction may be carried out under subatmospheric, atmospheric, and superatmospheric pressure conditions. However, atmospheric pressure conditions are generally used.

The present reaction is desirably conducted in the absence of water. It is frequently impossible, in a practical operation of this process, to insure that all of the reactants will be absolutely dry and the atmosphere in which the reaction is conducted is totally free of moisture. However, in the practical operation of the present process, water in an amount equivalent to that which could theoretically convert one weight percent of the maleic anhydride used in the reaction to maleic acid can be tolerated. This is preferably considered to be the maximum amount. In the usual case water is present in a relatively trace amount resulting in considerably less than 1 weight percent of the maleic anhydride being reacted to maleic acid.

To insure that the amount of water that gets into the reaction is as low as feasible, it is desirable to utilize an inert moisture free atmosphere in carrying out the reaction. This moisture free atmosphere can be provided by relatively dry gasses such as dry nitrogen, carbon dioxide, methane, helium, argon, and the like.

In carrying out the reaction, it is desirable to mix the reactants. The degree of mixing is not critical and gentle stirring of the reaction mass is sufficient. To avoid any complications in the reaction, it is desirable to effectively disperse the basic catalyst throughout the composition.

As pointed out in U.S. Pat. No. 3,784,586, in order to avoid premature reaction between the half esters and the ethylenically unsaturated monomer component, it is desirable to add polymerization inhibitors to the reaction mixture. These polymerization inhibitors include tertiary butyl catechol, hydroquinone monomethyl or monoethyl ether, benzoquinone, tertiary-butyl hydroquinone, methyl hydroquinone and mixtures thereof, such as mixtures of hydroquinone monomethyl ether and benzoquinone. These polymerization inhibitors are used in amounts of from about 30 to about 600 parts per million by weight.

The composition of this invention can be cured by free radical mechanisms such as, electron beam radiation, actinic radiation, azo and peroxide curing agents such as those which are described by Gallagher, et al "Organic Peroxides Review, Plastics Design & Processing," July, 1978, pages 38–42, and August, 1978, pages 60–67, inclusive. The technology disclosed in those two articles is incorporated herein by reference. The choice of the specific peroxide or azo initiators for the purpose of curing the composition of this invention is within the purview of those having skill in this art and the manner in which such peroxides and azo initiators operate to effect a desirable cure is generally characterized in the aforementioned articles.

Illustrative of a few such curing agents are 2,2'-azo-bis-isobutyronitrile, dibenzoyl peroxide, lauroyl peroxide, di-t-butyl peroxide, diisopropyl peroxide carbonate, t-butyl peroxy-2-ethylhexanoate, t-butylperpivalate, 2,5-dimethyl-hexane-2,5-di-per-2-ethyl hexoate, t-butylperoctate, t-butylperneodecanoate, t-butylperbenzoate, t-butylpercrotonate, t-butyl perisobutyrate, di-t-butyl perphthalate, and the like.

The concentration of the curing agent is not critical and can be varied within wide limits. As a representative range, the concentration can vary from about 0.25 to about 5.0 weight percent, preferably from about 0.5 to about 2.5 weight percent, and most preferably, from about 0.75 to about 2.0 weight percent, based on the weight of the reaction product (I), maleic anhydride and the ethylenically unsaturated monomer.

The compositions of this invention can be cured neat or in combination with fillers, pigments, fibers, such as fiberglass, carbon fibers and aromatic polyamide fibers (such as aramid fibers sold by E. I. DuPont Nemours, Wilmington, Del. and sold under the trademark Kevlar), hollow glass or phenolic resin spheres, and the like.

The compositions of this invention are particularly useful for the manufacture of rigid fiber reinforced molded articles. A preferred procedure for producing a molded article from this composition is described in copending U.S. patent application Ser. No. 035,011 entitled "Molding Process and Apparatus Therefore", and filed on May 1, 1979 in the name of R. Angell, Jr., which is incorporated herein by reference. In this application, a process for rapidly fabricating fiber reinforced thermoset resin articles is described. The fiber reinforcement is comprised of one or more fibers with a melting point or a transition temperature above about 130° C. The process comprises the steps of (a) providing in a heatable matched metal die mold, a bonded web of one or more of said fibers, (b) providing in an accumulator zone, a liquid body of a thermosettable organic material having a viscosity determined at 120° C., in the absence of curing agent therefore, of less than about 50 centipoises, and which is curable upon heating to a thermoset resin composition, the viscosity of said liquid body being maintained essentially constant in the accumulator zone by keeping its temperature below that at which curing of said materials is substantial, (c) closing said mold containing said web, (d) injecting at least a portion of said thermosettable organic material under pressure from said accumulator zone into the mold to thereby fill the cavity in said mold, (e) initiating the curing of said materials by subjecting the materials to a temperature by heating the mold, which is above the temperature at which the curing of said materials is initiated, and (f) opening said mold and removing the cured thermoset article therefrom. The fiber reinforcement may be from about 15 to about 80, preferably from about 30 to about 70 weight percent of the weight of the molded article which is removed from the mold.

Due to the low viscosities of the compositions of this invention, they readily flow through and about and within the total confines of the mold and the fibrous material contained therein to effect a uniform distribution of the reaction product within the ultimate molded product.

The compositions of this invention can also be used to impregnate fabrics, manufacture laid up laminate structures for use in electrical potting and casting processess to protect motors, windings, and the like.

The following examples serve to illustrate specific embodiments of this invention and it is not intended that the invention shall be limited by the examples.

COMPARATIVE EXAMPLE

This example is an attempt to duplicate Example 1 of U.S. Pat. No. 3,784,586.

A 4-necked, 2 liter round bottomed flask equipped with a paddle stirrer, glass tube for nitrogen addition, a nitrogen outlet, a thermometer, and an electric heating mantle was charged with 438 g of 2,2,4-trimethyl-1,3-pentanediol and 588 g of maleic anhydride. The solid mixture was melted and heated to a temperature of 80° over a 1 hour period. The temperature was maintained at 80° for four hours. The solution at this point was light tan and viscous. A sample was removed for analysis by titration methods and NMR spectroscopy.

Two titration methods were used to determine the acid number of the solution. The acid number is the milligrams of KOH needed to neutralize one gram of the sample.

In the first procedure, the solution was dissolved in aqueous pyridine and titrated against KOH. In the second, the acid number was determined by dissolving the solution in a pyridine and methanol mixture and titrating against KOH. The first procedure, using aqueous pyridine, determined maleic acid as the diacid, and the second procedure, using the mixture of pyridine and methanol, determined maleic acid as a mono-acid. The results of these two procedures showed that the acid number was 418 by the first procedure and 333 by the second procedure. The unreacted maleic anhydride content was determined by employing the following formula:

$$(100)\frac{(418 - 333)}{333} = \frac{8500}{333} = \begin{array}{l}25.5 \text{ mole \%}\\ \text{unreacted}\\ \text{maleic anhydride.}\end{array}$$

NMR analysis of the reaction product revealed the following distribution of maleic anhydride containing components:
70 percent maleates (maleate half esters, diesters, and maleic acid)
7 mole percent fumarates
23 mole percent unreacted maleic anhydride.

After the solution had been heated at 80° C. for four hours, it was treated with 714 g of styrene containing 268 mg of hydroquinone and 268 mg of methyl hydroquinone. It was allowed to stand at room temperature. The next day a casting was made from this composition.

Six days after the styrene had been added to the maleic anhydride/2,2,4-trimethyl 1,3-pentanediol reaction mixture, a white crystalline precipitate appeared in the bottom of the resin container. Seven days later a 1057 g portion of the mixture was filtered to recover the precipitate. The precipitate weighed 3.8 g and was identified as maleic acid by NMR spectroscopy. The clear yellow filtrate was allowed to stand at room temperature. Two days after the initial filtration, additional quantities of white precipitate were detected in the resin container.

A portion of the solution produced in the experiment, prior to the addition of styrene, was allowed to stand 16 days at room temperature. NMR analysis of the sample gave the following distribution of maleic anhydride containing components:

77 mole percent maleates (half esters and diesters),
7 mole percent fumarates,
8 mole percent unreacted maleic anhydride,
8 mole percent maleic acid.

EXAMPLE 1

A 1 liter, 3-necked flask fitted with a paddle stirrer, nitrogen inlet and outlet, a thermometer, and an electric heating mantle was charged with 288.8 g of molten 2,2,4-trimethyl-1,3-pentane diol and 387.8 g of molten maleic anhydride. The solution was warmed to 110° C. and maintained at that temperature for 3 hours. 0.1 g of hydroquinone was then added. The product, a clear amber liquid, was poured into a jar for storage. Three days later the product was a white, opaque semisolid. NMR analysis of the product in d₆-dimethylsulfoxide indicated that the maleic anhydride containing components possessed the following distribution:
8.3 mole percent maleic anhydride,
18.3 mole percent fumarate esters,
56.6 mole percent maleate esters (maleate half esters and diester),
16.7 mole percent maleic acid.

A portion of this product was dissolved in styrene. A copious white solid precipitated. It was identified as maleic acid by NMR analysis.

This experiment supports the statement in U.S. Pat. No. 3,784,586 that reaction temperatures in excess of 100° C. result in resins of inferior quality in that invention.

However, contrary to the inferences in U.S. Pat. No. 3,784,586, the poor quality (i.e. precipitate) is not due to the presence of fumarate groups in the resin, but to maleic acid. The large amount of maleic acid produced in this experiment results in a thermosetting resin with a low cross link density compared to a resin wherein esentially all of the anhydride is utilized to form crosslinkable oligomers.

EXAMPLE 2

A 3 liter, 3-necked round bottomed flask fitted with a paddle stirrer, nitrogen inlet, a heating mantle and a thermometer equipped with a Thermo-Watch controller was charged with 408.2 g of 2,2-dimethyl-3-hydroxypropyl 2,2-dimethyl-3-hydroxypropionate and 392.2 g of maleic anhydride. The mixture was warmed to melt the reactants. The temperature of the mixture was raised to 140° C. and maintained at that temperature by applying a cooling bath until the reaction exotherm subsided. The mixture was heated for an additional 30 minutes at 140° C. The mixture was then cooled to 80° C., treated with 0.32 g of hydroquinone, and transferred to a jar for storage. The yield was 1557 g (95%), indicating a 5% mechanical loss. The product was stored for 25 days. Analysis of the maleic anhydride components in the stored mixture by NMR spectroscopy indicated that 8 mole percent of the anhydride was unreacted, 88 mole percent was in the maleate form (maleic acid, mono-or diester), and 4 mole percent was in the fumarate form. The acid number of the resin was 303 mg KOH/g (in aqueous pyridine), indicating that the major portion of the maleic anhydride was present as the half acid ester. Less than 5 percent of the maleate containing species were maleic acid or maleate diesters.

The product obtained was a clear viscous liquid. A portion was mixed with styrene to give a clear solution containing 50 percent styrene by weight. Within 8 days, this solution contained a precipitate of maleic acid.

The product not containing styrene was a clear viscous liquid for more than 30 days.

EXAMPLE 3

A 4-necked, 3 liter flask equipped with a paddle stirrer, thermometer, a nitrogen inlet and outlet, and an electric heating mantle was charged with 614 g of the 2-mole ethoxylate of 2,2-bis(4-hydroxyphenyl) propane and 392.2 g (4.0 moles) of maleic anhydride. Titration of the ethoxylate indicated that 614 g contained 4.0 moles of hydroxyl groups. The mixture was heated to 120° C. and maintained at that temperature for one hour. The reaction mixture was then treated with 0.20 g of hydroquinone and cooled to room temperature. The product was a light amber clear viscous liquid. A 20 g portion of this material was blended with 20 g of styrene to afford a clear, low viscosity solution. The solution was allowed to stand at room temperature. After 8 days a precipitate of maleic acid was detected in the solution.

EXAMPLE 4

The apparatus as described in Example 3 was charged with 980.6 g of maleic anhydride and 670.9 of dipropylene glycol. The solution was warmed to 110° C., maintained at that temperature by applying a cooling bath to control the reaction exotherm, and then heated at 110°–120° C. for two hours. The clear solution was transferred to a jar for storage.

Analysis of the product nine days after its preparation gave the following distribution of maleic anhydride-derived components:
6 mole percent unreacted maleic anhydride,
91 mole percent maleates,
3 mole percent fumarates.

Less than 2 percent of the original charge of maleic anhydride was present as either maleate diesters or as maleic acid.

The product was stored for 60 days. Its appearance was unchanged. A sample was dissolved in styrene to form a solution containing 35 weight percent styrene. Within 10 days a precipitate of maleic acid was present in the bottom of the mixture containing styrene.

The above Examples describe the preparation of thermosetting compositions without the use of a base.

The following Examples describe the preparation of compositions wherein a basic compound is used. cl EXAMPLE 5

The apparatus of Example 3 was charged with 438 g of 2,2,4-trimethyl-1,3-pentanediol and 588 g of maleic anhydride. The mixture was warmed to 52° C. to give a clear colorless solution. 2.05 g of N-methylimidazole was then added. The reaction mixture immediately became brown and reached a maximum temperature of 80° C. after 23 minutes. The reaction mixture was maintained at 75° to 80° C. for 4.0 hours. At this point a sample was removed. NMR analysis indicated that the maleic anhydride containing components had the following distribution:
73.3 mole percent maleates (half ester, diesters and maleic acid),
4.7 mole percent fumarates,
22.0 mole percent maleic anhydride.
Less than 2 percent of the original maleic anhydride charged was present as either maleic acid or maleate diesters. With this amount of N-methylimidazole, the amount to unreacted maleic anhydride was essentially the same as that determined in the Comparative Example which did not utilize a catalyst.

The reaction mixture was separated into portions of 207.5 g and 820.5 g. The latter was mixed with 571 g of styrene containing 0.41 g of hydroquinone, and 0.2 g of benzoquinone. A clear brown homogeneous solution resulted. Its styrene content was 41 weight percent, the same as in the Comparative Example. The solution was stored at room temperature. Unlike the compositions of the previous Examples, a precipitate did not develop in this mixture. It remained a clear homogeneous solution for 42 days.

This example shows that a base, i.e., the amine containing component, is necessary in order to prevent the formation of maleic acid precipitate in the mixture containing styrene.

EXAMPLE 6

The apparatus of Example 3 was charged with 219 g of 2,2,4-trimethyl-1,3-pentane diol and 294 g of maleic anhydride. The mixture was warmed to 59° C. and 1.02 g of pyridine was added. The mixture immediately became dark brown. The temperature in the mixture reached a maximum of 72° C. after 12 minutes. Ten minutes later the reaction was cooled to 54 C. and an additional 4.10 g of pyridine was added. Intermittent application of heat raised the reaction temperature to 70° C. after 25 minutes. The solution temperature was maintained at 70° to 77° C. for the duration of the reaction. Samples were removed for analysis at 2 hours and at 4 hours after the addition of the first portion of the catalyst. The distribution of the maleic anhydride containing components in the solution was determined by NMR spectroscopy. The results were as follows:

| at 2 hr. | at 4 hr. | |
|---|---|---|
| 80 | 76 | mole percent maleates (half esters, diesters and maleic acid |
| 1 | 15 | mole percent fumarates |
| 19 | 9 | mole percent maleic anhydride |

Less than 2 percent of the original maleic anhydride charge was present as maleic acid or as maleate diesters. Following removal of the four hour sample for analysis, a solution of 357 g of styrene containing 0.13 g of hydroquinone and 0.13 g of benzoquinone was added. The resulting mixture was clear, brown and precipitate free. It was stored at room termperature for 31 days. Its appearance was unchanged.

This example shows that the free maleic anhydride content of a resin containing 2,2,4-trimethyl-1,3-pentanediol can be reduced to a low level prior to styrene addition by the appropriate choice of an amine catalyst.

EXAMPLE 7

A 3 liter, 4-necked flask fitted with a paddle stirrer, nitrogen inlet and outlet, and a thermometer was charged with 833.2 g of molten 2,2-dimethyl-3-hydroxypropyl 2,2-dimethyl-3-hydroxypropionate and 800 g of molten maleic anhydride. The mixture was rapidly stirred at 48° C. as 6.53 g of N-methylimidazole was added by syringe. The temperature of the reaction mixture gradually increased to a maximum of 95° C. over the next 23 minutes. During the next 37 minutes the temperature decreased to 75° C. At the end of this period, a sample of the viscous brown solution was removed for determination of free maleic anhydride using titrimetric procedures. Titrations indicated that the acid number of the reaction product was 281 in a pyridine/methanol mixed solvent and was 318 in an aqueous pyridine solvent. Therefore, the unreacted maleic anhydride content of the sample was 13.2 percent of the original charge. As soon as the samples were removed for the titration, a solution of 1336 g of styrene containing 0.44 g of hydroquinone and 0.44 g of benzoquinone was added. The final product was a brown homogeneous clear solution. The product was allowed to stand overnight at room temperature. The next morning its appearance was unchanged. Four days later about 20 percent of the product was in the form of a low melting solid precipitate. When the product was warmed to 50° C., the solid melted. The solid was a mixture of 2,2-dimethyl-3-hydroxypropyl 2,2-dimethyl-3-hydroxypropionate maleate half esters, maleic anhydride and styrene. No maleic acid precipitate was present in this product. The resin was stored as a solid solution at room temperature and was heated to about 50° C., to generate the clear, precipitate-free solution.

Alternatively mixtures which were liquid at room temperature were obtained by blending the product of this Example, the product Example 8, and sufficient styrene to give a mixture containing about 50 weight percent styrene. Homogeneous liquid mixtures were obtained when at least 25 percent of the diol component of the mixture was dipropylene glycol.

EXAMPLE 8

The apparatus as described in Example 7 was charged with 547.3 g of dipropylene glycol and 800 g of maleic anhydride. The mixture was warmed to 43° C. and 5.23 (0.4 weight percent) of N-methylimidazole was added by syringe to the rapidly stirred mixture. Immediately the reaction mixture changed from colorless to dark brown. The temperature of the mixture was raised to 120° C. over the next 18 minutes by the intermittent application of heat. Twenty minutes after addition of the catalyst, a sample was removed for analysis by titrimetric methods. The amount of unreacted maleic anhydride present was 23 percent of the original charge. The temperature of the reaction was gradually decreased from 120° C. to 63° C. over the next 60 minutes. At the end of this period, a sample was removed for NMR analysis and 0.31 g of hydroquinone was added. NMR analysis showed that the distribution of maleic anhydride containing products was as follows:

88 mole percent maleates (half ester, diesters, and maleic acid),
0.5 mole percent fumarates,
11.5 mole percent unreacted maleic anhydride. Less than 2 percent of the original maleic anhydride charged was present as either maleic acid or maleate diesters.

One minute after the addition of hydroquinone to the reaction mixture, a solution of 725 g of styrene containing 0.61 g of benzoquinone was added. The resulting product was a brown homogeneous precipitate-free solution. It was stored at room temperature. No precipitate was present in this solution for 30 days.

EXAMPLE 9

The apparatus as described in Example 3 was charged with 324.9 g (1.59 moles) of 2,2-dimethyl-3-hydroxypropyl 2,2-dimethyl-3-hydroxypropionate, 60.1 g (0.45 moles) of dipropylene glycol and 400 g (4.08 moles) of maleic anhydride. The mixture was warmed to 50° C., and then 3.15 g of N-methylimidazole was added to the rapidly stirred mixture. The temperature of the brown reaction solution increased from 50 to 100° C. in 6 minutes. Over the next hour, the temperature slowly decreased to 55° C. Samples were removed for titrations at 20 minute and 60 minute intervals after addition of the catalyst. The unreacted maleic anhydride remaining after 20 minutes was 20 percent, while at 60 minutes it was 11 percent of the original charge. The brown viscous solution was maintained at 55° to 68° C., after the second sample was removed, for an additional hour. Then 0.18 g hydroquinone, 0.18 g of benzoquinone, and 785 g of styrene was added to give a clear brown homogeneous one phase solution. The resin was allowed to stand at 26° C. It remained a precipitate-free, homogeneous liquid for more than 24 days.

EXAMPLE 10

The apparatus of Example 3 was charged with 292 g of 2,2,4-trimethyl-1,3-pentane diol and 392 g of maleic anhydride. The mixture was warmed to 60 and 6.85 g of sodium methoxide was added in portions over a 23 minute period. Intermittent application of heat raised the reaction temperature to 80° C. after 23 minutes. The solution temperature was maintained at 80° to 82° C. for the duration of the reaction. Samples were removed for analysis at 4.8 hours after the addition of the first portion of catalyst. The distribution of the maleic anhydride containing components in the solution was determined by NMR spectroscopy. The results were as follows:

| at 4 hr. | |
|---|---|
| 76 | mole percent maleates (half esters, diesters and maleic acid) |
| 13 | mole percent fumarates |
| 12 | mole percent maleic anhydride |

Less than 3 percent of the original maleic anhydride charge was present as maleic acid or as maleate diesters. Following removal of the sample for analysis, a solution of 476 g of styrene containing 0.29 g of methyl hydroquinone was added. The resulting mixture was clear, yellow and precipitate free. It was stored at room temperature for 60 days. Its appearance was unchanged.

This example shows that the free maleic anhydride content of a resin containing 2,2,4-trimethyl-1,3-pentanediol can be reduced to a low level prior to styrene addition by the appropriate choice of a basic catalyst.

EXAMPLE 11

A 10 gallon stainless steel reactor equipped with an agitator and an inert gas inlet and outlet was changed with 21.94 kg. of maleic anhydride. When the liquid anhydride was at 63° C., 9.98 kg of molten 2,2,4-trimethyl-1,3-pentanediol and 3.32 kg of propylene glycol were added, causing the temperature of the mixture to drop to 48° C. The mixture was then warmed to 55° C. and 17 g of N-methylimidazole was added with agitation. The mixture was warmed to 80° C. during the next 50 minutes. It was then cooled to 61° C. and treated with an additional 53 g of N-methylimidazole. The reaction mixture was warmed to 80° C., maintained at that temperature for 3 hr., and then discharged. The product was a viscous amber syrup which contained less than 15 percent of the original charge of maleic anhydride in unreacted form.

The product was allowed to stand for 2 days. A 1000 g portion was blended with 1000 g of styrene containing 0.50 g of methyl hydroquinone. The resulting amber solution remained free of precipitate for more than 30 days.

The following Examples 12 to 32 show the effect of various basic compounds on the reaction of maleic anhydride with 2,2-dimethyl-3-hydroxypropyl 2,2-dimethyl-3-hydroxypropionate.

EXAMPLE 12

A 125 ml Erlenmeyer flask was charged with 30.0 g of molten maleic anhydride and 31.2 g of molten 2,2-dimethyl-3-hydroxypropyl 2,2-dimethyl-3-hydroxypropionate and placed in an oil bath at 75°±10° C. The magnetically stirred solution was allowed to equilibrate to the bath temperature, 1.0 weight percent of 1,4-diazabicyclo[2.2.2]octane was added. After 10 minutes the reaction mixture was removed from the oil bath, cooled to room temperature, and analyzed by titration procedures to determine the amount of maleic anhydride reacted. 76 percent of the maleic anhydride reacted after 10 minutes.

The addition of maleic anhydride to 2,2-dimethyl-3-hydroxypropyl 2,2-dimethyl-3-hydroxypropionate is an exothermic reaction. The relative effectiveness of the catalyst was determined by recording the change in temperature of the reaction mixture after addition of catalyst. The most effective catalysts produced the largest exotherms.

Table I shows the type of catalyst, the amount of catalyst added to the reaction, the initial temperature, maximum temperature, the change in temperature (ΔT) and the time to reach maximum temperature.

EXAMPLES 13–32

The procedure of Example 12 was exactly repeated except that the types of catalysts and the amount thereof added to the reaction, as shown in Table I, was substituted for 1.0 weight percent of the 1,4-diazabicyclo[2.2.2]octane of Example 12.

The initial temperature, maximum temperature, the change in temperature (ΔT) and the time to reach maximum temperature are as set forth in Table I.

TABLE I

| Example | Catalyst (wt %) | Initial Temp (°C.) | Maximum Temp (°C.) | ΔT(°C.) | Time to reach Maximum Temp (min) |
|---|---|---|---|---|---|
| Control | None | 67 | 67 | 0 | — |
| 12 | 1,4 Diazabicyclo [2.2.2] octane (1.0) | 75 | 103 | 28 | 2.8 |
| 13 | O—[CH$_2$CH$_2$N(CH$_3$)$_2$]$_2$ (1.0) | 70 | 100 | 30 | 4.6 |
| 14 | 2.2 mole ethoxylate of aniline (1.0) | 75 | 83 | 8 | 7.0 |
| 15 | 4-(dimethylamino) pyridine (1.0) | 78 | 122 | 44 | 2.5 |
| 16 | Triethylamine (1.0) | 78 | 107 | 29 | 2.0 |
| 17 | 1-methylimidazole (1.0) | 78 | 124 | 46 | 1.3 |
| 18 | N,N dimethyltoluidine (1.0) | 67 | 88 | 21 | 6.4 |
| 19 | N,N dimethylaniline (1.0) | 67 | 74 | 7 | 9.5 |
| 20 | Pyridine (1.0) | 67 | 125 | 58 | 2.0 |
| 21 | 4-Vinylpyridine (0.5) | 70 | 105 | 35 | 2.8 |
| 22 | 2,6-dimethyl piperazine (1.0) | 70 | 108 | 38 | 2.0 |
| 23 | N,N-dimethyl piperidine (1.0) | 70 | 102 | 32 | 2.0 |
| 24 | 2-methylimidazole (1.0) | 69 | 102 | 33 | 4.5 |
| 25 | Sodium methoxide (1.0) | 72 | 108 | 36 | 2.5 |
| 26 | Titanium tetrabutoxide (1.0) | 78 | 82 | 4 | 6.0 |
| 27 | Potassium hydroxide (0.5)$^a$ | 67 | 84 | 17 | 7.2 |
| 28 | Sodium hydroxide (0.5)$^a$ | 68 | 86 | 18 | 5.9 |
| 29 | Sodium acetate (1.0)$^a$ | 66 | 89 | 23 | 3.2 |
| 30 | Potassium acetate (1.0)$^a$ | 68 | 93 | 25 | 3.8 |
| 31 | Lithium acetate (1.0)$^a$ | 67 | 94 | 27 | 3.9 |
| 32 | Magnesium oxide (1.0) | 76 | 110 | 34 | 2.0 |

$^a$The entire catalyst sample did not dissolve during the test.

The data of Table I shows that bases such as amines, metal alkoxides and oxides and metal salts of carboxylic acids are particularly effective catalysts for this invention.

The following Examples 33 to 45 show the preparation of half esters from polyols, maleic anhydride and catalyst, in styrene. For diols, the optimum amount of maleic anhydride reacted should be a minimum of 90 percent to obtain the compositions of this invention. Generally, a clear homogeneous liquid mixture was obtained at room temperature except as noted. None of the Examples contained a maleic acid precipitate.

EXAMPLE 33

A glass jar was charged with 122.9 g of styrene and 300 parts per million of hydroquinone inhibitor. To this was added 76.6 g of 2,2-dimethyl-3-hydroxypropyl 2,2-dimethyl-3-hydroxypropionate, and 73.6 g of maleic anhydride. 0.27 g of N-methylimidazole catalyst was then added. The initial temperature of the reaction mixture was 40° C. Samples of this mixture were taken periodically to determine the progress of the reaction by titration in a pyridine/methanol mixed solvent and in aqueous pyridine. The amount of maleic anhydride reacted after 67, 168 and 792 hours, after addition of catalyst was as follows:

| Time (hr) | Maleic anhydride reacted (percent) |
|---|---|
| 67 | 75 |
| 168 | 85 |
| 792 | 92 |

EXAMPLE 34

A glass jar was charged with 99.5 g of styrene and 300 parts per million of hydroquinone inhibitor. To this was added 62.0 g of 2,2-dimethyl-3-hydroxypropyl 2,2-dimethyl-3-hydroxypropionate, 59.0 g of maleic anhydride. 0.44 g of N-methylimidazole catalyst was then added to the solution. The initial temperature of the reaction mixture was 38° C. and the maximum temperature was 40° C. Samples were removed periodically to determine the progress of the reaction by titration in a pyridine/methanol mixed solvent and in aqueous pyridine. The amount of maleic anhydride reacted after 65, 168 and 650 hours, after addition of catalyst was as follows:

| Time (hr.) | Maleic anhydride reacted (percent) |
|---|---|
| 65 | 80 |
| 168 | 89 |
| 650 | 93 |

A solid mixture melting at about 50° C. formed after 650 hours. The melted product was a clear liquid.

EXAMPLE 35

A glass jar was charged with 36.4 g of styrene and 300 parts per million of hydroquinone inhibitor. To this was added 22.7 g of 2,2-dimethyl-3hydroxypropyl 2,2-dimethyl-3-hydroxypropionate and 21.8 g of maleic anhydride and 0.80 g of N-methylimidazole catalyst. The initial temperature of the reaction mixture was 37° C. and the maximum temperature was 52° C. Samples were removed periodically to determine the progress of the reaction by titration in a pyridine/methanol mixed solvent and in aqueous pyridine. The amount of maleic anhydride reacted after 0.6, 19, 49 and 144 hours after addition of the catalyst was as follows:

| Time (hr.) | Maleic anhydride reacted (percent) |
|---|---|
| 0.6 | 73 |
| 19 | 91 |
| 49 | 94 |
| 144 | 96 |

This mixture was a homogeneous solution for over 80 days.

EXAMPLE 36

A glass jar was charged with 81.1 g of styrene and 300 parts per million of t-butyl catechol inhibitor. To this was added 40.2 g of dipropylene glycol, and 58.8 g of maleic anhydride, followed by 0.49 g of N-methylimidazole catalyst. The initial temperature of the reaction mixture was 31° C. and the maximum temperature was 35° C. Samples were removed periodically to determine the progress of the reaction by titration in a pyridine/methanol mixed solvent and in aqueous pyridine. The amount of maleic anhydride reacted after 72, 140 and 385 hours after addition of catalyst was as follows:

| Time (hr.) | Maleic anhydride reacted (percent) |
|---|---|
| 72 | 66 |
| 140 | 78 |
| 385 | 90 |

After 320 hours, the solution separated into two clear liquid phases. The upper phase was essentially styrene. The lower phase contained the maleic anhydride/dipropylene glycol reaction product, unreacted maleic anhydride, and styrene. The styrene content of the lower phase was 40 weight percent.

EXAMPLE 37

A glass jar was charged with 84.0 g of styrene and 300 parts per million of t-butyl catechol inhibitor. To this was added 43.9 g of 2,2,4-trimethyl1,3-pentanediol and 58.8 g maleic anhydride. 0.49 g of N-methylimidazole catalyst was then added to the solution. The initial temperature of the reaction mixture was 33° C. and the maximum temperature was 36° C. Samples were removed periodically to determine the progress of the reaction by titration in a pyridine/methanol mixed solvent and in aqueous pyridine. The amount of maleic anhydride reacted after 72, 504 and 870 hours and 65 days after addition of catalyst was as follows:

| Time (hr.) | Maleic anhydride reacted (percent) |
|---|---|
| 72 | 67 |
| 504 | 90 |
| 870 | 93 |
| 65 days | 95 |

After 65 days a casting was made from this mixture. The composition was a homogeneous, precipitate-free solution for over 80 days.

EXAMPLE 38

A glass jar was charged with 84.0 g of styrene and 300 parts per million of t-butyl catechol inhibitor. To this was added 43.9 g of 2-ethyl-1,3-hexanediol and 58.8 g of maleic anhydride. 0.49 g of N-methylimidazole catalyst was then added. The initial temperature of the reaction mixture was 29° C. and the maximum temperature was 34° C. Samples were removed periodically to determine the progress of the reaction by titration in a pyridine/methanol mixed solvent and in aqueous pyridine. The amount of maleic anhydride reacted after 166 and 504 hours after addition of catalyst was as follows:

| Time (hr.) | Maleic anhydride reacted (percent) |
|---|---|
| 166 | 85 |
| 504 | 93 |

The composition was a homogeneous amber liquid at room temperature for over 80 days.

EXAMPLE 39

A glass jar was charged with 136.5 g. of styrene and 300 parts per million of t-butyl catechol inhibitor. To this was added the polycaprolactone ester of trimethylol propane containing 3.6 moles of caprolactone and 58.8 g of maleic anhydride. 0.49 g. of N-methylimidazole catalyst was then added to the solution. The initial temperature of the reaction mixture was 29° C. and the maximum temperature was 31° C. Samples were removed periodically to determine the progress of the reaction by titration in a pyridine/methanol mixed solvent and pyridine. The amount of maleic anhydride reacted after 140 hours after addition of catalyst was as follows:

| Time (hr.) | Maleic anhydride reacted (percent) |
|---|---|
| 140 | 88 |

EXAMPLE 40

A glass jar was charged with 25.0 g. of styrene and 300 parts per million of benzoquinone inhibitor. To this was added a mixture of 10.2 g. of 2,2-dimethyl-3-hydroxypropyl 2,2-dimethyl-3-hydroxypropionate, 5.2 g of 2,2-dimethyl-1,3 propanediol and 19.6 g of maleic anhydride. 1.0 g. of N-methylimidazole catalyst was then added to the solution. The initial temperature of the reaction mixture was 25° C. and the maximum temperature was 27° C. Samples were removed periodically to determine the progress of the reaction by titration in a pyridine/methanol mixed solvent and pyridine. The amount of maleic anhydride reacted after 90 hours after addition of catalyst was as follows:

| Time (hr.) | Maleic anhydride reacted (percent) |
|---|---|
| 90 | 92 |

EXAMPLE 41

A glass jar was charged with 64.9 g of styrene and 300 parts per million of benzoquinone inhibitor. To this was added 21.9 g of 2,2,4-trimethyl-1,3-pentanediol, 3.8 g of 1,2-propylene glycol and 39.2 g of maleic anhydride. 1.0 g of N-methylimidazole catalyst was then added to the solution. The initial temperature of the reaction mixture was 25° C. and the maximum temperature was 28° C. Samples were removed periodically to determine the progress of the reaction by titration in a pyridine/methanol mixed solvent and in aqueous pyridine. The amount of maleic anhydride reacted after 91 and 139 hours after addition of catalyst was as follows:

| Time (hr.) | Maleic anhydride reacted (percent) |
|---|---|
| 91 | 86 |
| 139 | 92 |

EXAMPLE 42

A glass jar was charged with 66.4 g of styrene and 300 parts per million of benzoquinone inhibitor. To this was added 21.9 g of 2,2,4-trimethyl-1,3-pentanediol, 5.3 g of diethylene glycol, and 39.2 g of maleic anhydride. 1.0 g of N-methylimidazole catalyst was then added to the solution. The initial temperature of the reaction mixture was 25° C. and the maximum temperature was 28° C. Samples were removed periodically to determine the progress of the reaction by titration in a pyridine/methanol mixed solvent and in aqueous pyridine. The amount of maleic anhydride reacted after 90 hours after addition of catalyst was as follows:

| Time (hr.) | Maleic anhydride reacted (percent) |
|---|---|
| 90 | 90 |

EXAMPLE 43

A glass jar was charged with 14.8 g of styrene and 300 parts per million of benzoquinone inhibitor. To this was added 15.0 g of polypropylene glycol with a molecular weight, (Mn) of 150, and 19.6 g of maleic anhydride. 0.5 g of N-methylimidazole catalyst was then added to the solution. The initial temperature of the reaction mixture was 25° C. and the maximum temperature was 26° C. A sample was removed to determine the progress of the reaction by titration in a pyridine/methanol mixed solvent and in pyridine. The amount of maleic anhydride reacted after 118 hours after addition of catalyst was 92 percent.

EXAMPLE 44

A homogeneous liquid mixture was obtained from the following:
46.0 g of the 2-mole ethoxylate of 2,2-bis (4-hydroxyphenyl) propane,
5.2 g of 2,2-dimethyl-1,3-propanediol,
39.2 g of maleic anhydride,
48.7 g of styrene,
1.4 g of N-methylimidazole, and
40 mg of benzoquinone The mixture was agitated for 1 day and then allowed to stand at room temperature. Three days later the brown homogeneous liquid was analyzed by titrimetric methods. It was determined that 94 percent of the original charge of maleic anhydride had reacted.

EXAMPLE 45

A homogeneous liquid mixture was obtained from the following:
34.6 g of the 2-mole propoxylate of 2,2-bis (4-hydroxyphenyl) propane,
10.4 g of 2,2-dimethyl-1,3-propanediol,
39.2 g of maleic anhydride,
45.3 g of styrene,
1.3 g of N-methylimidazole, and
40 mg of benzoquinone.

The mixture was agitated for 1 day and then allowed to stand at room temperature. Five days later the brown homogeneous liquid as analyzed by titrimetric methods. It was determined that 90 percent of the original charge of maleic anhydride had reacted.

EXAMPLE 46

A series of six castings were prepared by blending several of the compositions of the Examples, as identified in Table II, with one percent by weight of an initiator as shown in Table II. The solutions were poured into a 10×10×⅛ inch glass mold and heated at 65° C. for 16 hours and then postcured at 128° C. for 6 hours. The castings were clear and hard.

Table II lists the Example by which the resin was prepared, the method of preparing the resin, the polyol reacted, styrene content, type and amount of catalyst, type of initiator and Barcol hardness (as measured by ASTM D-2583).

In the Table, the method of preparing the resin is identified as follows:

A—The polyol and maleic anhydride (and catalyst, if present) were heated at 50° to 100° C. prior to adding styrene.

B—The polyol, maleic anhydride and catalyst were reacted at <52° C. in styrene.

C—The polyol and maleic anhydride were heated at 110°±5° C. for 2 hours prior to styrene addition.

TABLE II

| | Casting | | | | | |
|---|---|---|---|---|---|---|
| | 1 | 2 | 3 | 4 | 5 | 6 |
| Example | Comparative Example | 5 | 6 | 37 | 2 | 35 |
| Method of Preparation | A | A | A | B | C | B |
| Polyol (1) | TMPD | TMPD | TMPD | TMPD | ED | ED |
| Styrene content (wt. %) | 41 | 41 | 41 | 45 | 45 | 45 |
| Amine catalyst | None | N-methylimidazole | Pyridine | N-methylimidazole | None | N-methylimidazole |
| Amount of catalyst (wt. %) | 0 | 0.12 | 0.6 | 0.26 | 0 | 1.0 |
| Initiator (2) | I | II | I | I | II | I |
| Barcol Hardness | 43 | 49 | 46 | 49 | 43 | 45 |

(1) TMPD is 2,2,4-trimethyl-1,3-pentanediol  ED is 2,2-dimethyl-3-hydroxypropyl 2,2-dimethyl-3-hydroxypropionate
(2) I is 1-t-butylazo-1-cyanocyclohexane  II is t-butyl perbenzoate

EXAMPLE 47

Pieces of the castings prepared in Example 46 were immersed overnight at room temperature in the solvents indicated in Table III. The degree of solvent swelling was determined by comparison of the weights of the pieces before and after solvent immersion. For 2,2,4-trimethyl-1,3-pentanediol, castings containing amines had reduced swelling compared to the casting prepared from the composition described in U.S. Pat. No. 3,784,586. A reduced degree of swelling was also observed for the casting made with 2,2-dimethyl-3-hydroxypropyl 2,2-dimethyl-3-hydroxypropionate containing an amine compared to the 2,2-dimethyl-3-hydroxypropyl 2,2-dimethyl-3-hydroxypropionate casting without the amine.

Table III lists the Example by which the resin was prepared, styrene content, type and amount of catalyst and the weight gain on immersion for 16 hours in toluene, acetone and methylene chloride.

EXAMPLE 48

Pieces of the castings prepared in Example 46 were immersed in boiling water for two hours to determine their water sorption characteristics. The weight increase resulting from the two hour water boil exposure was used to measure water sorption. As shown in the Table those castings containing amines showed smaller weight increases than the casting made from the composition of U.S. Pat. No. 3,784,586.

Table IV lists the Example by which the resin was prepared, styrene content, the type and amount of amine catalyst used and the percent of weight gained after a 2 hour water boil.

TABLE IV

| Example | Comparative Example | 5 | 6 | 37 |
|---|---|---|---|---|
| Diol (1) | TMPD | TMPD | TMPD | TMPD |
| Styrene content (wt. %) | 41 | 41 | 41 | 45 |
| Amine Catalyst | None | N-methylimidazole | Pyridine | N-methylimidazole |
| Amount of catalyst (wt. %) | None | 0.12 | 0.61 | 0.26 |
| Weight gain after 2 hr. water boil (%) | 3.2 | 2.4 | 1.9 | 2.2 |

(1)TMPD is 2,2,4-trimethyl-1,3-pentanediol

EXAMPLE 49

A sample of the composition of Example 7 was warmed at 48° C. to convert from a solid mass to an amber low viscosity precipitate-free solution.

A homogeneous liquid mixture was prepared by mixing:

100 g of the composition of Example 7,
60 g of the composition of Example 39,
0.8 g of Zelec UN, and
1.6 g of t-butyl perbenzoate.

This mixture was injected into a web of 1 inch glass fibers weighing 119 g in 20 seconds. The mold was heated to 140° C. The pressure in the mold ranged from 30 psi to 200 psi. After 5 minutes the pressure in the

TABLE III

| Example | Comparative Example | 5 | 6 | 37 | 2 | 35 |
|---|---|---|---|---|---|---|
| Diol(b) | TMPD | TMPD | TMPD | TMPD | ED | ED |
| Styrene content (wt. %) | 41 | 41 | 41 | 45 | 45 | 45 |
| Amine Catalyst | None | N-methylimidazole | Pyridine | N-methylimidazole | None | N-methylimidazole |
| Amount of catalyst (wt. %) | None | 0.12 | 0.6 | 0.26 | None | 1.0 |
| Weight gain (%) | | | | | | |
| Toluene | 0.6 | 0.2 | 0 | 0.2 | 0.2 | 0 |
| Acetone | 13.7(a) | 5.8 | 9.9 | 2.9 | 10.1 | 4.1 |
| Methylene Chloride | 19.3 | 10.5 | 15.0 | 9.1 | 65.6 | 33.6 |

(a)Sample showed partial disintegration.
(b)TMPD = 2,2,4-trimethyl-1,3-pentanediol  ED = 2,2-dimethyl-3-hydroxypropyl 2,2-dimethyl-3-hydroxypropionate mold was released. Then the mold was opened, and a glass reinforced composite part was removed. The flexural strength and flexural modulus of the part are listed in Table V. The glass content of the composite article was determined to be 65 weight percent by ashing the sample.

EXAMPLE 50

A liquid mixture was prepared by mixing the following:
100 g of the composition of Example 6,
6.1 g of diethylene glycol, and
11.2 g of maleic anhydride.
The homogeneous liquid mixture was stirred at 26° C. for 16 hr. Then, 0.6 g of Zelec UN mold release and 1.2 g of 1-t-butylazo-1-cyanocyclohexane were added. Six hours later this composition was injected into a web of glass fibers in a heated mold and cured in exactly the same manner as in Example 49. The properties of the composite part are listed in Table V.

EXAMPLE 51

A liquid mixture was prepared from the following
100 g of the composition of Example 6,
4.3 of propylene glycol,
11.2 g of maleic anhydride.
The homogeneous liquid mixture was stirred at 26° C. for 16 hr. Then 0.6 g of Zelec UN and 1.2 g of 1-t-butylazo-1-cyanocyclohexane were added. Six hours later the composition was injected into a web of glass fibers in a heated mold and cured in exactly the same manner as in Example 49. The properties of the composite part are listed in Table V.

EXAMPLE 52

A polymerizable homogeneous liquid mixture was prepared by mixing 550 g of the composition of Example 9 with 2.75 g of Zelec UN mold release (an organophosphate mold release agent sold by E.I. duPont de Nemours, Wilmington, Del.) and 5.50 g of t-butyl perbenzoate. A portion of this mixture was injected in 20 seconds into a heated mold containing a web of glass fibers weighing 108 grams. After 3 minutes the mold was opened and a composite part containing 55 percent by weight glass fibers was removed. The flexural strength and flexural modulus mesured on 1×4×1/8 inch test specimens are listed in Table V.

EXAMPLE 53

A polymerizable homogeneous liquid mixture was prepared by mixing:
150 g of the composition of Example 6,
0.75 g of Zelec UN mold release, and
1.50 g of 1-t-butylazo-1-cyanocyclohexane.
A composite part was formed from this mixture as described in Example 49.

TABLE V

| Example | 49 | 50 | 51 | 52 | 53 |
|---|---|---|---|---|---|
| Composite Properties | | | | | |
| Glass content (wt. %) | 65 | 64 | 62 | 55 | 62 |
| Cure time (min.) | 5 | 5 | 5 | 3 | 5 |
| Flexural strength (psi) | 59,500 | 25,000 | 36,100 | 35,700 | 30,700 |
| Flexural modulus (psi) | 2,470,000 | 1,460,000 | 1,790,000 | 1,470,000 | 1,460,000 |

The data in the Table V shows that the compositions of this invention can be effectively utilized to produce composite articles with high strength and stiffness.

What is claimed is:

1. A composition comprising a homogeneous liquid mixture of:
   (a) a half ester of an organic polyol characterized by the following empirical formula:

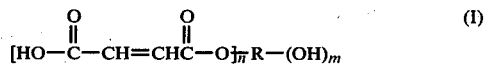

$$[\text{HO}-\overset{\overset{\text{O}}{\|}}{\text{C}}-\text{CH}=\text{CH}\overset{\overset{\text{O}}{\|}}{\text{C}}-\text{O}]_n\text{R}-(\text{OH})_m \qquad (I)$$

wherein n is a number having an average value of about 1.8 to less than about 4, m is equal to the free valence of R less the average value of n, R is the hydroxyl-free residue of an organic polyol which contained from 2 to 4, inclusive, hydroxyl groups, OH, in formula (I),
   (b) maleic anhydride,
   (c) an ethylenically unsaturated monomer which forms a liquid homogeneous mixture with and is copolymerizable with (a) and (b), and
   (d) a basic compound.

2. A composition as in claim 1 wherein the organic polyol comprises a mixture of polyols.

3. A composition as in claim 2 wherein the mixture of polyols contains 2,2,4-trimethyl-1,3-pentanediol.

4. A composition as in claim 3 which contains propylene glycol.

5. A composition as in claim 3 which contains a polycaprolactone ester of a polyol wherein from abou 1 to about 5 moles of caprolactone are esterified with the polyol.

6. A composition as in claim 5 which contains a polycaprolactone ester of trimethylol propane wherein about 3.6 moles of caprolactone are esterified with trimethylol propane.

7. A composition as in claim 2 wherein the mixture of polyols contains 2,2-dimethyl-3-hydroxypropyl 2,2-dimethyl-3-hydroxypropionate.

8. A composition as in claim 7 which contains a polycaprolactone ester of a polyol wherein from about 1 to about 5 moles of caprolactone are esterified with the polyol.

9. A composition as in claim 8 which contains the polycaprolactone ester of trimethylol propane where about 3.6 moles of caprolactone are esterified with trimethylol propane.

10. A composition as in claim 7 wherein the polyol contains dipropylene glycol.

11. A composition as in claim 2 wherein the mixture of polyols contains the 2-mole ethoxylate of 2,2-bis(4-hydroxyphenyl)propane.

12. A composition as in claim 11 wherein the polyol contains 2,2-dimethyl-1,3-propanediol.

13. A composition as in claim 2 wherein the mixture of polyols contains the 2-mole propoxylate of 2,2-bis(4-hydroxyphenyl)propane.

14. A composition as in claim 13 wherein the polyol contains 2,2-dimethyl-1,3-propanediol.

15. A composition as in claim 1 wherein the maleic anhydride content does not exceed a total of about 10 mole percent of the amount of maleic anhydride used in producing the half ester (a).

16. A composition as in claim 1 which contains a mole ratio of half ester to maleic anhydride of about 9:1 to about 200:1.

17. A composition as in claim 1 which contains a mole ratio of ethylenically unsaturated monomer to half ester of from about 0.6:1 to about 6:1.

18. A composition as in claim 1 wherein the basic compound is selected from an amine or a metal salt of an alcohol or carboxylic acid or a metal oxide or hydroxide.

19. A composition as in claim 18 wherein the basic compound is a secondary or tertiary amine.

20. A composition as in claim 19 wherein the amine has a $pK_b$ in the range of 3 to 12.

21. A composition as in claim 18 wherein 1 gram of the basic compound when dissolved in 100 milliters of water has a pH greater than 7.

22. A composition as in claim 1 wherein the monoethylenically unsaturated monomer is selected from styrene, α-methylstyrene, vinyl toluene and the lower alkyl esters of acrylic acid and methacrylic acid.

23. A composition as in claim 22 wherein monoethylenically unsaturated monomer is styrene.

24. A composition as in claim 1 which contains a polymerization inhibitor.

25. A process for preparing the composition of claim 1 which comprises
   (a) reacting maleic anhydride and an organic polyol in the presence of a base at a temperature of from about 40° C. to about 160° C. until about 70 percent of the maleic anhydride has reacted,
   (b) lowering the temperature to below about 120° C. and
   (c) adding an ethylenically unsaturated monomer and a polymerization inhibitor to the reaction mass.

26. A process for preparing the composition of claim 1 which comprises reacting maleic anhydride, an organic polyol and an ethylenically unsaturated monomer in the presence of a base and a polymerization inhibitor at a temperature of less than about 60° C.

27. A cured molded article prepared from the composition of claim 1.

28. A cured molded article as in claim 1 wherein the molded article contains from about 15 to about 80 weight percent, of the weight of the molded article, of one or more fibers with a melting point or a glass transition temperature above about 130° C.

29. A cured molded article as in claim 28 wherein the molded article contains from about 30 to about 70 weight percent, of the weight of the molded article of one or more fibers with a melting point or a glass transition temperature above about 130° C.

30. A cured molded article as in claim 28 or 29 wherein the fiber is glass.

* * * * *